US012797014B2

(12) United States Patent
Iguchi et al.

(10) Patent No.: US 12,797,014 B2
(45) Date of Patent: Nov. 17, 2026

(54) PROGRAM, INFORMATION PROCESSING METHOD, INFORMATION PROCESSING APPARATUS, AND MODEL GENERATION METHOD

(71) Applicant: TERUMO KABUSHIKI KAISHA, Tokyo (JP)

(72) Inventors: Akira Iguchi, Mishima (JP); Yusuke Seki, Tokyo (JP); Yuki Sakaguchi, Isehara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 722 days.

(21) Appl. No.: 17/953,581

(22) Filed: Sep. 27, 2022

(65) Prior Publication Data

US 2023/0012527 A1 Jan. 19, 2023

Related U.S. Application Data

(63) Continuation of application No. PCT/JP2021/009280, filed on Mar. 9, 2021.

(30) Foreign Application Priority Data

Mar. 27, 2020 (JP) ................................ 2020-058997

(51) Int. Cl.

*A61B 5/00* (2006.01)
*G06T 7/00* (2017.01)

(Continued)

(52) U.S. Cl.

CPC .......... *A61B 5/7275* (2013.01); *A61B 5/7267* (2013.01); *G06T 7/0012* (2013.01);

(Continued)

(58) Field of Classification Search

CPC ...... A61B 34/10; A61B 2034/101-108; A61B 34/25; A61B 2034/252; A61B 2034/254; A61B 2034/256; A61B 5/7275

See application file for complete search history.

(56) References Cited

U.S. PATENT DOCUMENTS

| | | | |
|---|---|---|---|
| 2011/0245650 | A1 | 10/2011 | Kerwin et al. |
| 2015/0038860 | A1 | 2/2015 | Fonte et al. |

(Continued)

FOREIGN PATENT DOCUMENTS

| | | | |
|---|---|---|---|
| CN | 110742633 | A | 2/2020 |
| EP | 2 977 922 | A2 | 1/2016 |

(Continued)

OTHER PUBLICATIONS

The extended European Search Report issued Jul. 25, 2023, by the European Patent Office in corresponding European Patent Application No. 21774718.7-1126. (9 pages).

(Continued)

*Primary Examiner* — Raphael Schwartz
(74) *Attorney, Agent, or Firm* — Buchanan Ingersoll & Rooney PC

(57) ABSTRACT

A non-transitory computer-readable medium (CRM) storing computer program code executed by a computer processor that executes a process, an information processing apparatus, and a model generation method that outputs complication information for a medical treatment. The process includes acquiring a medical image obtained by imaging a lumen organ of a patient before treatment, inputting the acquired medical image into a trained model so as to output complication information on a complication that is likely to occur after the treatment when the medical image is received, and outputting the complication information. Preferably, complication information including a type of the complication that is likely to occur and a probability value (Continued)

indicating an occurrence probability of the complication of the type is output.

20 Claims, 10 Drawing Sheets

(51) Int. Cl.

| | |
|---|---|
| ***G06V 10/22*** | (2022.01) |
| ***G06V 10/764*** | (2022.01) |
| ***G06V 10/774*** | (2022.01) |
| ***G16H 30/40*** | (2018.01) |

(52) U.S. Cl.
CPC ............ *G06V 10/22* (2022.01); *G06V 10/764* (2022.01); *G06V 10/774* (2022.01); *G16H 30/40* (2018.01); *G06T 2207/10064* (2013.01); *G06T 2207/10072* (2013.01); *G06T 2207/20081* (2013.01); *G06T 2207/30101* (2013.01); *G06V 2201/031* (2022.01)

(56) References Cited

U.S. PATENT DOCUMENTS

| | | | | |
|---|---|---|---|---|
| 2015/0087957 | A1 | 3/2015 | Liu et al. | |
| 2015/0367145 | A1 | 12/2015 | Sjölund et al. | |
| 2017/0035514 | A1* | 2/2017 | Fox | G06Q 10/10 |
| 2017/0076014 | A1* | 3/2017 | Bressloff | A61F 2/915 |
| 2018/0315182 | A1 | 11/2018 | Rapaka et al. | |
| 2019/0021677 | A1 | 1/2019 | Grbic et al. | |
| 2019/0198169 | A1 | 6/2019 | T et al. | |
| 2019/0244347 | A1 | 8/2019 | Buckler et al. | |
| 2019/0350550 | A1 | 11/2019 | Zhu et al. | |
| 2021/0251577 | A1* | 8/2021 | Itu | A61B 5/346 |

FOREIGN PATENT DOCUMENTS

| | | | |
|---|---|---|---|
| EP | 3 716 207 | A1 | 9/2020 |
| JP | 2014200549 | A | 10/2014 |

OTHER PUBLICATIONS

International Search Report (PCT/ISA/210) with translation and Written Opinion (PCT/ISA/237) mailed on May 25, 2021, by the Japan Patent Office as the International Searching Authority for International Application No. PCT/JP2021/009280. (8 pages).

Chinese Office Action dated Feb. 19, 2025, issued in Chinese Patent Application No. 2021800245971, with machine translation. (12 pages).

Chinese Search Report dated Feb. 18, 2025, issued in Chinese Patent Application No. 2021800245971. (3 pages).

* cited by examiner

FIG. 3

| COMPLICATION ID | COMPLICATION NAME | CATEGORY | COUNTERMEASURE INFORMATION |
|---|---|---|---|
| 10001 | RUPTURE OF CORONARY ARTERY | HEMORRHAGIC COMPLICATION | ·PLEASE PAY ATTENTION TO BALLOON SIZE DURING PRE-INFLATION<br>· WHEN BALLOON CANNOT BE FULLY INFLATED DURING PRE-INFLATION, PLEASE CONSIDER USING DEVICE SUCH AS ROTABLATOR |
| 10002 | DISSOCIATION AND HEMATOMA | HEMORRHAGIC COMPLICATION | ·PLEASE CONSIDER INDWELLING AT POSITION WHERE STENT EDGE DOES NOT COME TO PORTION HAVING PLAQUE<br>·PLEASE CONSIDER REVIEWING STENT SIZE<br>·WHEN STENT INDWELLING POSITION CANNOT BE CHANGED, PLEASE CONSIDER<br>–REDUCTION OF BALLOON INFLATED PRESSURE TO EDGE<br>–STENT INDWELLING IN ACCORDANCE WITH SIZE OF DISTAL BLOOD VESSEL<br>–USING SHORT BALLOON TO AVOID BALLOON INFLATION TO EDGE AND ACHIEVE POST-DILATION ONLY IN STENT |
| 10003 | PLAQUE SHIFT | SIDE BRANCH OCCLUSION | ·PLEASE CONSIDER SIDE BRANCH PROTECTION BY WIRE<br>·PLEASE CONSIDER PERFORMING KISSING BALLOON TECHNIQUE (KBT)<br>·PLEASE CONSIDER USING DIRECTIONAL CORONARY ATHERECTOMY (DCA) DEVICE |
| 10004 | CARINA SHIFT | SIDE BRANCH OCCLUSION | ·PLEASE CONSIDER SIDE BRANCH PROTECTION BY WIRE<br>·PLEASE CONSIDER PERFORMING KISSING BALLOON TECHNIQUE (KBT) |
| 10005 | PERIPHERAL EMBOLISM | PERIPHERAL EMBOLISM | ·PLEASE CONSIDER USING PERIPHERAL PROTECTION DEVICE |
| ... | ... | ... | ... |

PROGRAM, INFORMATION PROCESSING METHOD, INFORMATION PROCESSING APPARATUS, AND MODEL GENERATION METHOD

CROSS-REFERENCES TO RELATED APPLICATIONS

This application is a continuation of International Application No. PCT/JP2021/009280 filed on Mar. 9, 2021, which claims priority to Japanese Application No. 2020-058997 filed on Mar. 27, 2020, the entire content of both of which is incorporated herein by reference.

TECHNOLOGICAL FIELD

The present disclosure generally relates to a program, an information processing method, an information processing apparatus, and a model generation method.

BACKGROUND DISCUSSION

In a medical field, complications caused by medical practices such as surgery and examination can become a problem. Accordingly, various systems for supporting prevention of the complications have been proposed.

For example, Japanese Patent Application Publication No. 2014-200549A discloses a medical image processing apparatus that detects a region of surrounding tissue existing around an aortic valve of a heart based on a medical image captured by an X-ray computed tomography (CT) apparatus, arranges a model image of a prosthetic valve to be replaced with the aortic valve in the medical image, and evaluates a risk of a complication based on a distance between the region of the surrounding tissue and the model image of the prosthetic valve.

However, in the disclosure according to Japanese Patent Application Publication No. 2014-200549A, it cannot be said that an evaluation of the risk of the complication by simple pattern matching based on the distance in the image is necessarily accurate.

SUMMARY

A non-transitory computer-readable medium, an information processing method, an information processing apparatus, and a model generation method, are disclosed that are capable of suitably evaluating a risk of a complication.

A non-transitory computer-readable medium (CRM) storing computer program code executed by a computer processor that executes a process for outputting complication information is disclosed. The process includes acquiring a medical image obtained by imaging a lumen organ of a patient before treatment, inputting the acquired medical image into a trained model that is trained to output complication information on a complication that is likely to occur after the treatment, and outputting the complication information.

An information processing apparatus is disclosed, which comprises: an acquisition unit configured to acquire a medical image obtained by imaging a lumen organ of a patient before treatment; and an output unit configured to input the acquired medical image into a trained model that is learned to output complication information on a complication that is likely to occur after the treatment, and output the complication information.

A model generation method executed by a computer is disclosed, the model generation method comprising: acquiring training data including a medical image obtained by imaging a lumen organ of a patient before treatment and complication information on a complication that occurs after the treatment; and generating, based on the training data, a trained model that outputs the complication information when the medical image is received.

In one aspect, a risk of a complication can be suitably evaluated.

BRIEF DESCRIPTION OF THE DRAWINGS

FIG. 3 is a diagram illustrating an example of a record layout of a countermeasure information database (DB).

DETAILED DESCRIPTION

Figure 1:
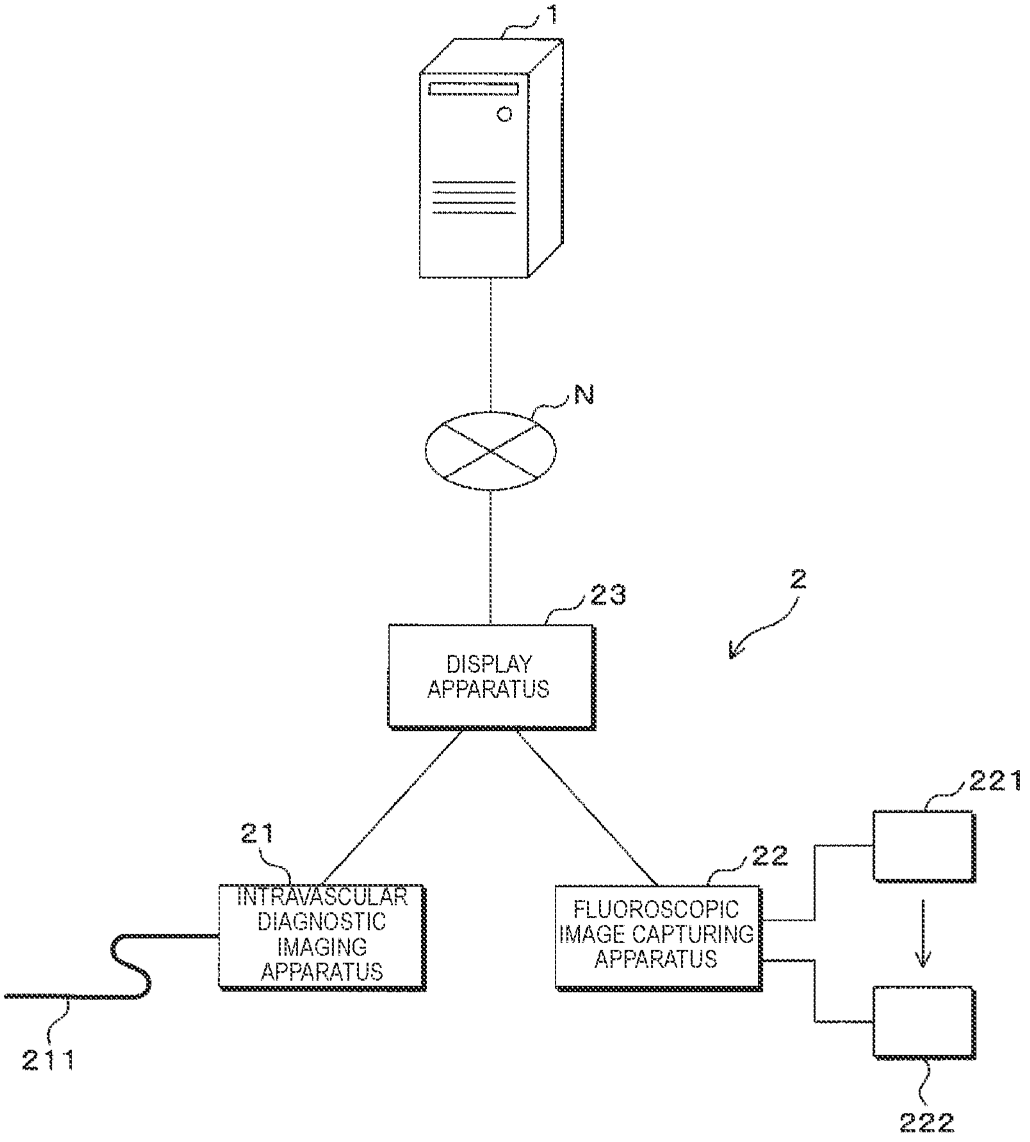
FIG. 1 is a diagram illustrating a configuration example of a treatment support system.

Set forth below with reference to the accompanying drawings is a detailed description of embodiments of a program, an information processing method, an information processing device, and a model generating method. Note that since embodiments described below are preferred specific examples of the present disclosure, although various technically preferable limitations are given, the scope of the present disclosure is not limited to the embodiments unless otherwise specified in the following descriptions. For convenience of explanation, dimensions in the drawings may be exaggerated and may be different from actual dimensions.

First Embodiment

FIG. 1 is a diagram illustrating a configuration example of a treatment support system. In the embodiment, the treatment support system will be described, which outputs complication information on a complication that is likely to occur after treatment based on a medical image obtained by imaging a blood vessel of a patient on whom intravascular treatment is performed. The treatment support system can include an information processing apparatus 1 and a diagnostic imaging system 2. The information processing apparatus 1 and the diagnostic imaging system 2 can be communicably connected to a network N such as a local area network (LAN) or the Internet.

In the present embodiment, the intravascular treatment is described as an example, but a lumen organ as a target is not limited to a blood vessel, and may be, for example, another lumen organ such as a bile duct, a pancreatic duct, a bronchus, or an intestine.

The diagnostic imaging system 2 can include an intravascular diagnostic imaging apparatus 21, a fluoroscopic image capturing apparatus 22, and a display apparatus 23. The intravascular diagnostic imaging apparatus 21 is an apparatus for imaging an intravascular tomographic image of the patient, and can be, for example, an intravascular ultrasound (IVUS) apparatus that performs an ultrasonic examination using a catheter 211. The catheter 211 is a medical instrument to be inserted into the blood vessel of the patient, and includes an imaging core that transmits ultrasound and receives a reflected wave from the inside of the blood vessel. The intravascular diagnostic imaging apparatus 21 generates an ultrasound tomographic image (transverse tomographic image) based on a signal of the reflected wave received by the catheter 211, and displays the ultrasound tomographic image on the display apparatus 23.

In the present embodiment, the intravascular diagnostic imaging apparatus 21 generates an ultrasound tomographic image, and may also generate an optical coherence tomographic image by an optical method such as optical coherence tomography (OCT) or optical frequency domain imaging (OFDI).

The fluoroscopic image capturing apparatus 22 is an apparatus unit for capturing a fluoroscopic image in which a body of the patient is seen through, and can be, for example, an angiography apparatus that performs an angiographic examination. The fluoroscopic image capturing apparatus 22 can include an X-ray source 221 and an X-ray sensor 222, and generates an X-ray fluoroscopic image by the X-ray sensor 222 receiving X-rays emitted from the X-ray source 221. For example, an X-ray opaque marker is attached to a distal end of the catheter 211 to enable position alignment with a tomographic image generated by the intravascular diagnostic imaging apparatus 21.

As described above, examples of a medical image include an ultrasound tomographic image, an optical coherence tomographic image and an angiographic image, and the medical image may also be a computed tomography (CT) image, a magnetic resonance imaging (MRI) image, or the like.

The information processing apparatus 1 is an information processing apparatus capable of processing various types of information and transmitting and receiving information, and can be, for example, a server computer, or a personal computer. In the present embodiment, the information processing apparatus 1 is a server computer, and hereinafter, the information processing apparatus 1 is read as a server 1 for the sake of conciseness. The server 1 may be a local server installed in the same facility (hospital or the like) as the diagnostic imaging system 2, or may be a cloud server communicably connected via the Internet or the like. Based on the medical image (tomographic image and fluoroscopic image) of the patient on whom the intravascular treatment is performed, the server 1 functions as a treatment support apparatus that outputs complication information on a complication that is likely to occur after the treatment. Specifically, as will be described later, the server 1 performs machine learning using predetermined training data, and prepares, in advance, a learning model 50 (see FIG. 4) that receives a medical image as input and outputs complication information. The server 1 inputs the medical image of the patient to be treated into the training model 50, and acquires the complication information from the training model 50. The server 1 outputs the complication information acquired from the training model 50 to the diagnostic imaging system 2, and causes the display apparatus 23 to display the complication information.

The complication information is a prediction result on the complication that is likely to occur due to the intravascular treatment, and can be information for assisting a user (health care worker) who treats a patient from a viewpoint of preventing complications. In the present embodiment, the intravascular treatment is an example, and a prediction result of the complication that is likely to occur due to percutaneous coronary intervention (PCI) using the catheter 211 is output as the complication information. For example, the complication information can include, in addition to a type of the complication that is highly likely to occur and a probability value of the type of the complication that is highly likely to occur, a prediction result of occurrence conditions of the complication, such as a treatment device that may cause the complication and use conditions of the treatment device. The treatment device can be, for example, a stent indwelled in a blood vessel, a balloon used for inflating a blood vessel, and is a device to be inserted into a blood vessel of a patient.

In addition, the server 1 can detect a dangerous region in which the complication is likely to occur based on the medical image, generate a second medical image indicating the detected dangerous region, and cause the display apparatus 23 to display the second medical image. The dangerous region can be, for example, a corresponding portion of a blood vessel in which the complication is highly likely to occur, and is a specific image region in the medical image. The server 1 can detect the dangerous region based on the medical image using the training model 50, generate the second medical image in which the dangerous region can be identified by a method such as color display, and cause the display apparatus 23 to display the second medical image.

Although the server 1 can perform processing using the training model 50 in the present embodiment, the training model 50 constructed by the server 1 may also be installed in the diagnostic imaging system 2 such that the processing may be locally executed.

Figure 2:
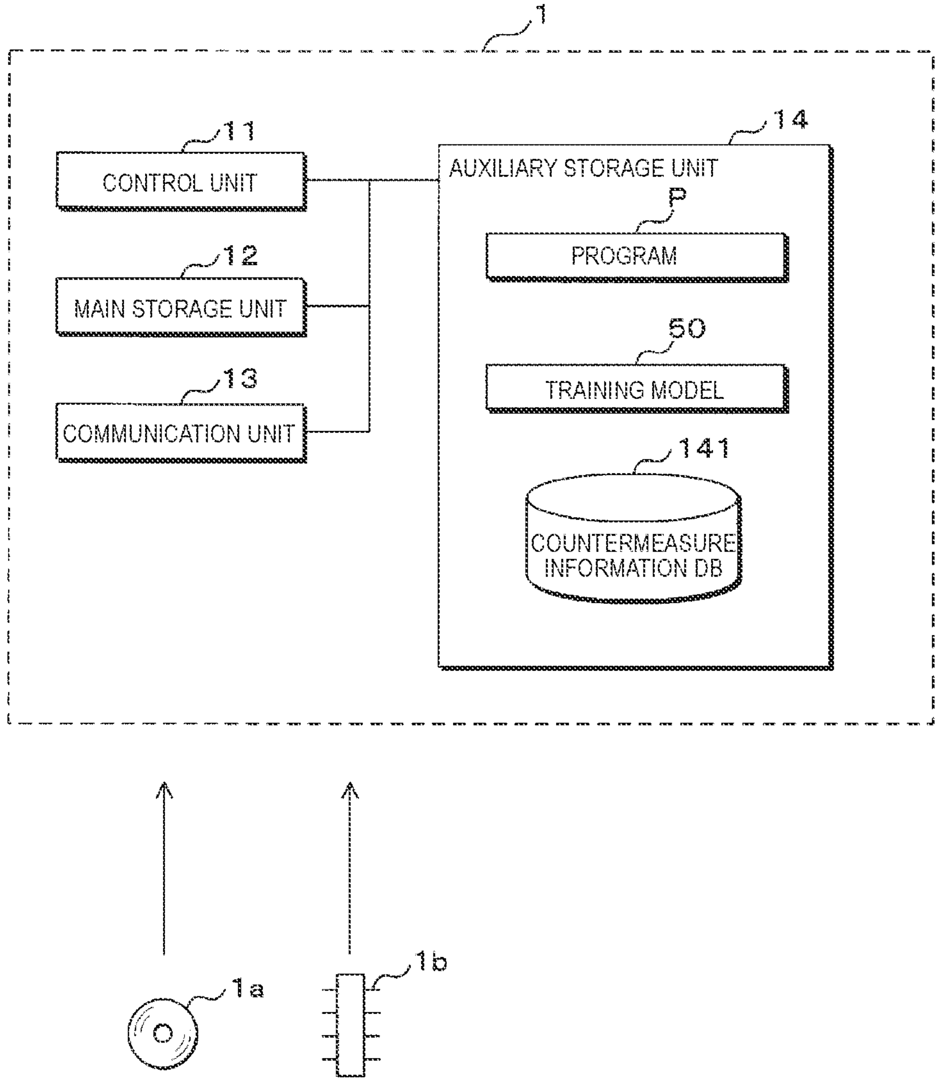
FIG. 2 is a block diagram showing a configuration example of a server.

FIG. 2 is a block diagram showing a configuration example of the server 1. The server 1 can include a control unit 11, a main storage unit 12, a communication unit 13, and an auxiliary storage unit 14. The control unit 11 can include one or more arithmetic processing devices such as a central processing unit (CPU), a micro-processing unit (MPU), and a graphics processing unit (GPU), and performs various types of information processing, control processing, and the like by reading and executing a program P stored in the auxiliary storage unit 14. The main storage unit 12 can be a temporary storage area such as a static random-access memory (SRAM), a dynamic random-access memory (DRAM), or a flash memory, and can temporarily store data necessary for the control unit 11 to execute arithmetic processing. The communication unit 13 can be a communication module for performing processing related to communication, and transmits and receives information to and from the outside of the server 1.

The auxiliary storage unit 14 can be a nonvolatile storage area such as a large-capacity memory or a hard disk, and stores the program P necessary for the control unit 11 to execute processing and other data. In addition, the auxiliary storage unit 14 stores the training model 50 and a countermeasure information database (DB) 141. The training model 50 is a model of machine learning that is trained using the training data as described above, and is a model that receives a medical image as input and outputs the complication information on the complication that is likely to occur after the treatment. The training model 50 can be used as a program module forming artificial intelligence software. The countermeasure information DB 141 is a database that stores countermeasure information for complications. In the present embodiment, the server 1 predicts the complication using the training model 50, and presents, for example, to the user, the countermeasure information for the complication that is highly likely to occur.

The auxiliary storage unit 14 may be an external storage device connected to the server 1. The server 1 may be a multi-computer including a plurality of computers, or may be a virtual machine virtually constructed by software.

In the present embodiment, the server 1 is not limited to the configuration described above, and may include, for example, an input unit that receives operation input, and a display unit that displays an image. In addition, the server 1 may include a reading unit that reads a portable storage medium 1*a* such as a compact disk (CD), a digital versatile disc (DVD), or a universal serial bus (USB) memory, and may read and execute the program P from the portable storage medium 1*a*. Alternatively, the server 1 may read the program P from a semiconductor memory 1*b*.

FIG. 3 is a diagram illustrating an example of a record layout of the countermeasure information DB 141. The countermeasure information DB 141 can include a complication identifier (ID) column, a complication name column, a category column, and a countermeasure information column. The complication ID can store complication IDs for identifying complications that are likely to occur due to the intravascular treatment. The complication name column, the category column, and the countermeasure information column can store names, categories, and countermeasure information of the complications in association with the complication IDs, respectively.

Figure 4:
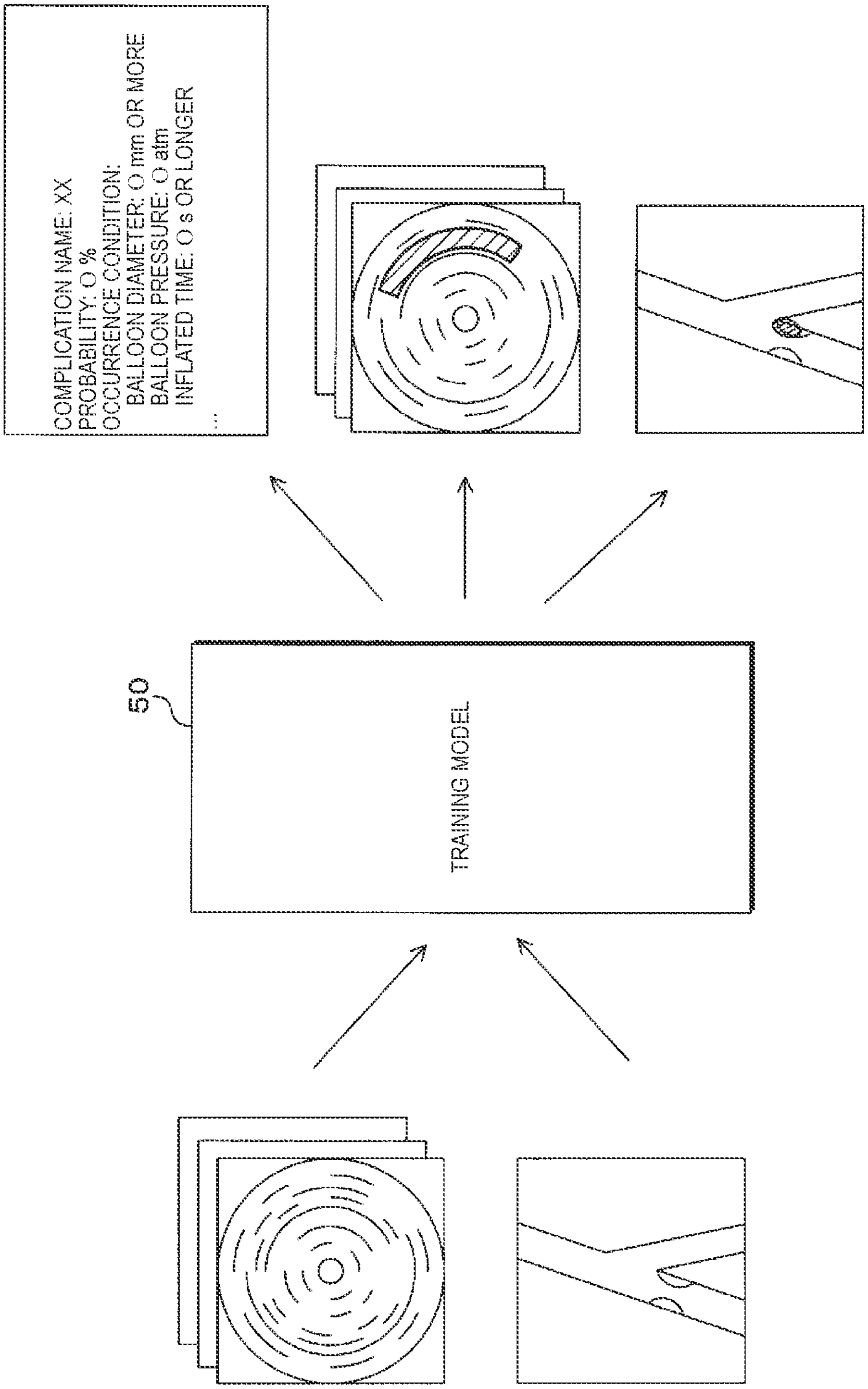
FIG. 4 is a diagram illustrating an outline of a training model.

FIG. 4 is a diagram illustrating an outline of the training model 50. The training model 50 is a model of machine learning that receives the medical image imaged in the diagnostic imaging system 2 as the input and outputs the complication information on the complication that is likely to occur after the treatment. The server 1 performs the machine learning using the predetermined training data to generate the training model 50 in advance. Then, the server 1 inputs the medical image acquired from the diagnostic imaging system 2 into the training model 50, and outputs the complication information.

As shown in FIG. 4, the training model 50 receives an ultrasound tomographic image (transverse tomographic image) imaged by the intravascular diagnostic imaging apparatus 21 and a fluoroscopic image captured by the fluoroscopic image capturing apparatus 22 as input. Then, the training model 50 outputs an estimation result estimated for items shown in an upper right part of FIG. 4 as the complication information.

For example, the training model 50 can output a probability value for each of a plurality of types of complications as one of estimation items. The server 1 performs learning using case data on the plurality of types of complications as training data, and prepares the training model 50 that estimates a probability value representing a probability of occurrence of each type of complication.

A complication to be estimated is not particularly limited, and representative examples of the complication associated with PCI include a hemorrhagic complication, side branch occlusion, and peripheral embolism. The hemorrhagic complication can include a rupture of a blood vessel, dissociation of a blood vessel wall, and the like. For example, when a balloon is inflated in a lesion where unevenly distributed calcified tissue is present, the blood vessel may be ruptured. In addition, when the stent is expanded at a portion having a plaque, the dissociation of the blood vessel wall or a rupture of the plaque is likely to occur due to an edge of the stent.

The side branch occlusion can be a complication that occludes a side branch blood vessel by treating a main trunk (main branch). When the balloon is inflated or the stent is indwelled at a bifurcated portion where the main trunk and the side branch diverge, an inlet portion of the side branch may be compressed and blocked.

The peripheral embolism can be a complication in which a thrombus or the like occurs due to mechanical stimulation of the intravascular treatment and a peripheral artery is embolized. For example, when the balloon is inflated or the stent is indwelled for an unstable plaque (plaque including lipid components or inflammatory cells), contents of the plaque may flow out due to the mechanical stimulation and the thrombus is likely to occur.

The training model 50 estimates the probability value representing the probability of occurrence of each type of complication based on the medical image, and outputs the probability value as the complication information. The above complications are examples, and the complication to be estimated is not limited to the complications based on the medical image, and the outputs of the probability value as the complication information as disclosed herein.

In addition, the complication information can include an estimation result related to occurrence conditions of the complication. Specifically, the training model 50 estimates the treatment device that may cause the complication or the use conditions of the treatment device. As described above, the treatment device can be, for example, a balloon used for inflating a blood vessel, and a stent indwelled in a blood vessel, and can be a device to be inserted into a blood vessel. The treatment device is not limited to the balloon and the stent, and may be, for example, a rotablator for resection of a lesion.

For example, as shown in the upper right part of FIG. 4, the training model 50 can estimate an inflated diameter, an inflated pressure, an inflated time, and the like of the balloon in which the complication is highly likely to occur. In addition to the use conditions, the training model 50 may estimate information (for example, diameter and length of stent, type and length of balloon) on the treatment device itself in which the complication is highly likely to occur.

The training model 50 outputs the probability value, the occurrence conditions, and the like of each type of complication as the complication information, generates the second medical image by processing the dangerous region in which the complication is likely to occur with respect to the input medical image, and outputs the second medical image as one piece of complication information. The second medical image is a medical image showing an image region in which a risk of occurrence of the complication is high, and is an image in which a dangerous region is displayed in a display mode different from that of other image regions as shown by hatching on a right side of FIG. 4. For example, as shown in FIG. 4, the training model 50 generates a tomographic image and a fluoroscopic image in which a semitransparent mask of a display color other than black and white is superimposed on a tomographic image and a fluoroscopic image represented by black and white, and causes the display apparatus 23 to display the tomographic image and the fluoroscopic image.

It is preferable that the training model 50 changes the display mode (display color) of the dangerous region according to the type of complication corresponding to the dangerous region. Accordingly, the user can rather easily grasp which complication the dangerous region presented in the second medical image corresponds to.

Figure 5:
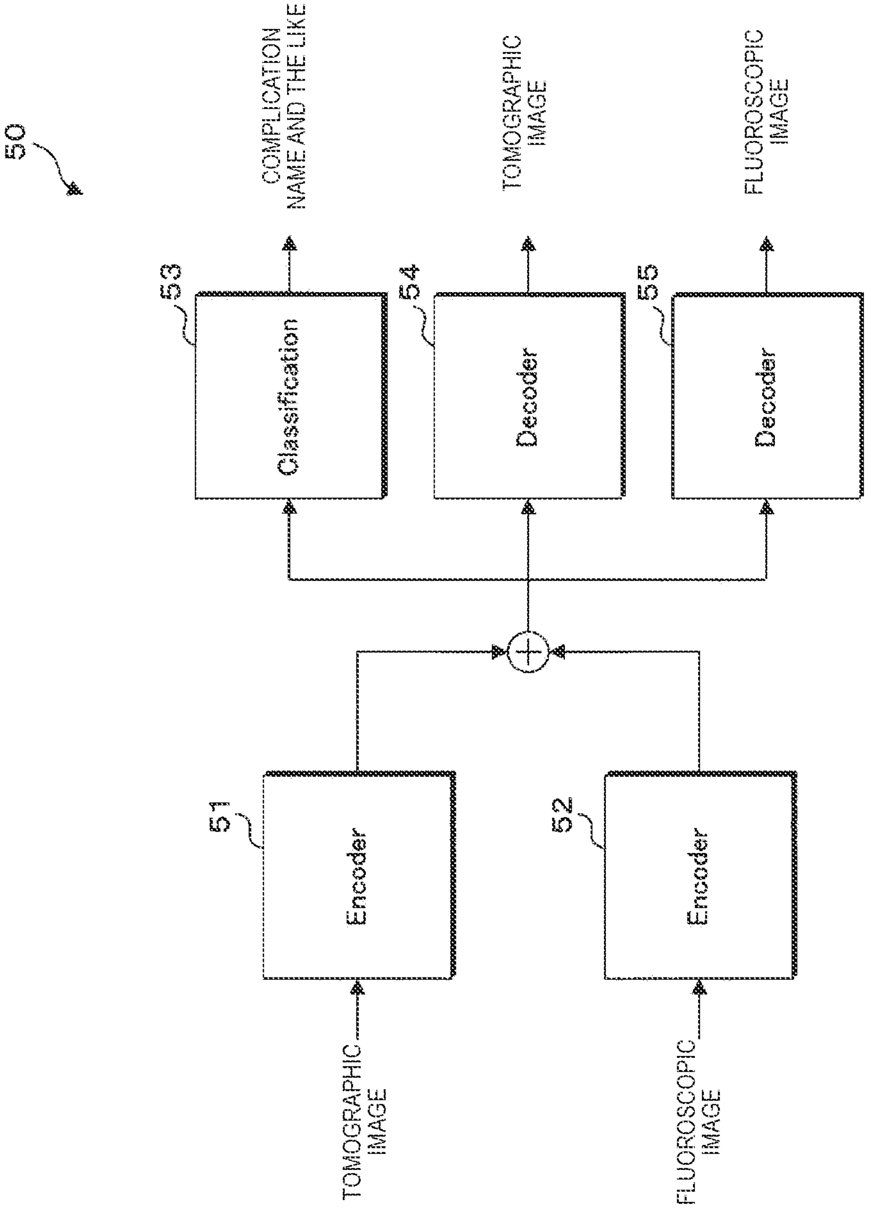
FIG. 5 is a diagram illustrating details of the training model.

FIG. 5 is a diagram illustrating details of the training model 50. FIG. 5 shows an example of a network configuration of the training model 50.

For example, the training model 50 can be a neural network generated by deep learning, and is a convolutional neural network (CNN) that extracts feature data of an input image by a large number of convolutional layers. The training model 50 includes an intermediate layer (hidden layer) in which a convolution layer that convolutes pixel information of the input image and a pooling layer that maps the convoluted pixel information are alternately connected, and extracts the feature data (feature data map) of the input image. The training model 50 outputs the complication information based on the extracted feature data.

Although the training model 50 is described as a CNN in the present embodiment, the training model 50 may be, for example, another neural network such as a recurrent neural network (RNN), or another model of machine learning such as a generative adversarial network (GAN), a support vector machine (SVM), or a decision tree.

The training model 50 according to the present embodiment can include a first encoder 51, a second encoder 52, a classifier 53, a first decoder 54, and a second decoder 55. Each of the first encoder 51 and the second encoder 52 can be an encoder that receives input of the tomographic image acquired from the intravascular diagnostic imaging apparatus 21 and the fluoroscopic image acquired from the fluoroscopic image capturing apparatus 22, and is an extractor that extracts the feature data of the input image by a large number of convolutional layers. Each of the first encoder 51 and the second encoder 52 performs convolution of the tomographic image and the fluoroscopic image, and extracts feature data of each image.

The classifier 53 can be a classifier that performs classification based on the feature data extracted by the first encoder 51 and the second encoder 52, and is an estimator that estimates the complication information other than the second medical image, such as a probability value and occurrence conditions of the complication. For example, the server 1 combines the feature data of the images extracted by the first encoder 51 and the second encoder 52, inputs the combined feature data into the classifier 53, and causes the classifier 53 to estimate the probability value of each type of complication and the like.

Each of the first decoder 54 and the second decoder 55 is a detector that detects the dangerous region from the tomographic image and the fluoroscopic image, and can be, for example, a decoder according to semantic segmentation (U-net or the like). The first decoder 54 and the second decoder 55 detect the dangerous region in pixel units from the tomographic image and the fluoroscopic image based on the feature data extracted by the first encoder 51 and the second encoder 52.

The semantic segmentation is a type of CNN, and is a type of encoder-decoder model that generates output data based on input data. The semantic segmentation can include, in addition to the convolution layer that compresses data of the input image, a deconvolution layer that maps (enlarges) feature data obtained by compression to an original image size. The deconvolution layer identifies which object is present at which position in the image in pixel units based on the feature data extracted by the convolution layer, and generates a label image generated by binarizing which object the pixel corresponds to.

Each of the first decoder 54 and the second decoder 55 includes a large number of deconvolution layers, and generates the label image generated by binarizing the dangerous region for each of the tomographic image and the fluoroscopic image. For example, the server 1 combines the feature data of the tomographic image and the fluoroscopic image extracted by the first encoder 51 and the second encoder 52, inputs the combined feature data into the first decoder 54 and the second decoder 55 respectively, and causes the first decoder 54 and the second decoder 55 to generate the label image.

The semantic segmentation is used to detect the dangerous region in the present embodiment, and other object detection models such as Region CNN (R-CNN) and You Only Look Once (YOLO) may also be used.

The configuration of the training model 50 illustrated in FIG. 5 is an example, and the present embodiment is not limited to the training model illustrated in FIG. 5. For example, the server 1 may separately prepare a model for estimating the probability value or the like of the complication and a model for detecting the dangerous region. In addition, a model for detecting a dangerous region (semantic segmentation) and a model for estimating a probability value or the like may be connected in series, and a detection result of the dangerous region in the former model may be input into the latter model, so that the detection result of the dangerous region may be used for estimating a probability value or the like of the complication. In this way, the configuration of the training model 50 can be changed appropriately.

The server 1 uses the training data to which correct complication information is assigned as label data (metadata) to perform learning on the medical image for training. For example, the server 1 uses data of a plurality of patients in whom the complication occurs after the treatment as the training data. In the training data, the intravascular tomographic image and the fluoroscopic image of the patient in whom the complication occurs are assigned with label data. The label data indicates the type of the complication that occurs in the patient, the occurrence conditions (inflated diameter, inflated pressure, inflated time, and the like of balloon) when the complication occurs, and the region (dangerous region) in the medical image in which the complication occurs.

The training data may include not only the data of the patient in whom the complication occurs but also the data of the patient in whom the complication does not occur. In addition, the training data is not limited to data of an actual patient, and may also be virtual data increased by a data generation unit such as GAN.

The server 1 inputs the tomographic image and the fluoroscopic image for training into the first encoder 51 and the second encoder 52 to extract the feature data, and inputs the extracted feature data into the classifier 53, the first decoder 54, and the second decoder 55 to output the complication information. The server 1 compares the output complication information with the correct complication information, and optimizes a parameter such as a weight between neurons so that the two pieces of complication information are approximate to each other. Accordingly, the server 1 generates the training model 50.

When the complication information is actually output for the patient to be treated, the server 1 acquires the medical image of the patient to be treated from the diagnostic imaging system 2, inputs the medical image into the training model 50, and outputs the complication information. As shown in FIG. 4, the server 1 acquires tomographic images of a plurality of consecutive frames along a longitudinal direction of the blood vessel from the intravascular diagnostic imaging apparatus 21 and acquires a fluoroscopic image captured at a time of generating the tomographic images from the fluoroscopic image capturing apparatus 22 in accordance with scanning of the catheter 211. The server 1 inputs the tomographic images of the plurality of frames into the first encoder 51, inputs the fluoroscopic image into the second encoder 52, and outputs the complication information to the display apparatus 23.

The server 1 may also input and process the tomographic images of the plurality of frames one by one into the training model 50, but it is preferable that the tomographic images of the plurality of consecutive frames are collectively input and the complication information can be estimated based on the tomographic images of the plurality of frames. In this case, for example, the training model 50 can be configured as a 3D-CNN (for example, 3D-U-net), and the tomographic images of the plurality of frames are handled as three-dimensional data in which coordinates of two-dimensional tomographic images are set as two axes and time points (generation time points) at which the tomographic images of the frames are acquired are set as one axis. The server 1 inputs the tomographic images (for example, 16 frames) for a predetermined unit time into the training model 50 as a set, and predicts the complication information based on the tomographic images of the plurality of frames.

Alternatively, the server 1 may set the training model 50 as a model obtained by combining the CNN and the RNN, and insert a long-short term memory (LSTM) layer that stores the feature data of the tomographic images of the frames into a rear side of the encoder, so that the complication information may be predictable based on the feature data of the tomographic images of the plurality of frames. By collectively processing the tomographic images of the plurality of consecutive frames, it is possible to improve prediction accuracy in consideration of not only a tomographic image at a certain position but also tomographic images at positions before and after the certain position.

Figure 6:
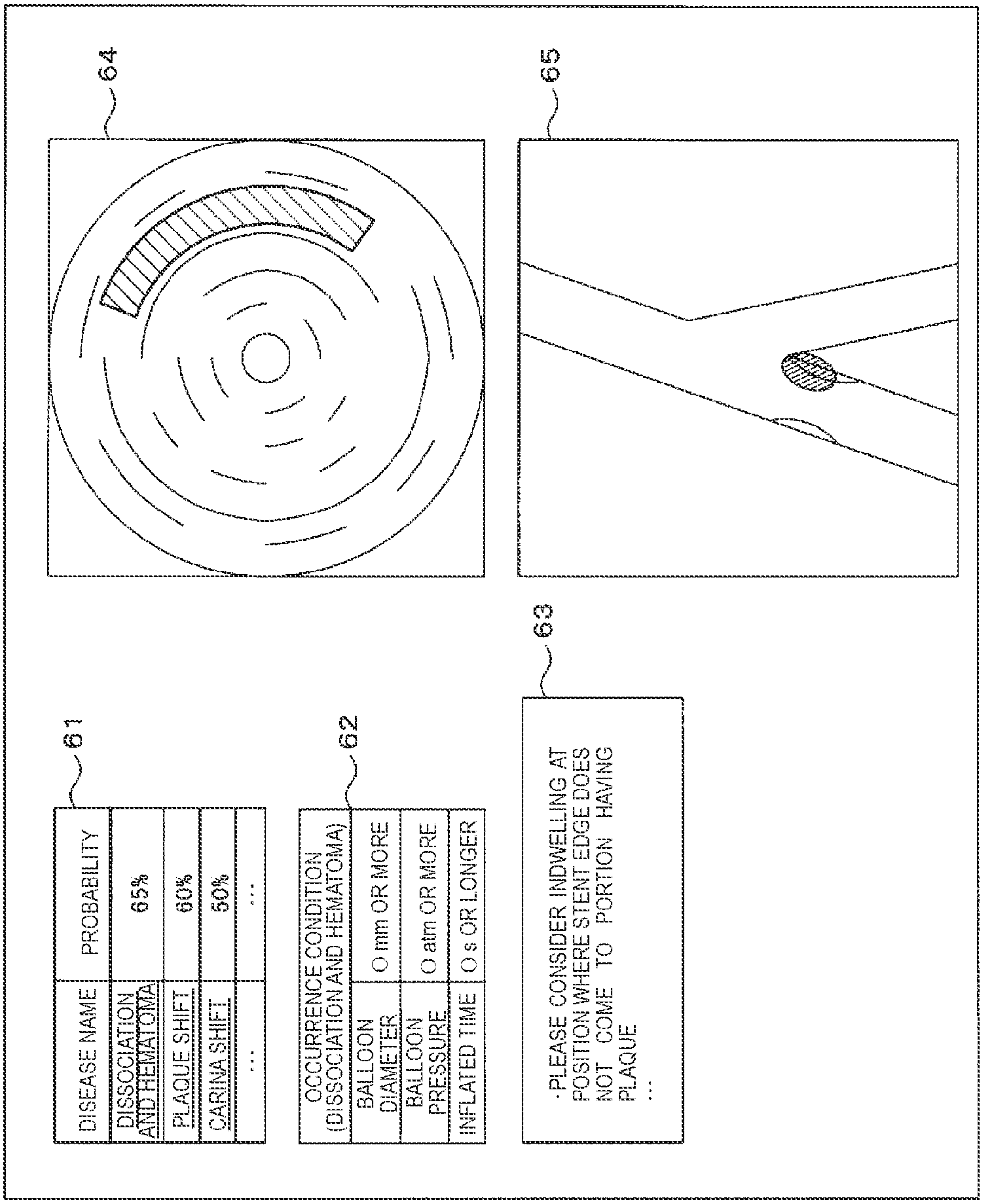
FIG. 6 is a diagram illustrating an example of a display screen that displays complication information.

FIG. 6 is a diagram illustrating an example of a display screen that displays the complication information. FIG. 6 shows the example of the display screen that displays the complication information output from the server 1. The screen can include a complication list 61, an occurrence condition list 62, a countermeasure information column 63, a tomographic image 64, and a fluoroscopic image 65.

The complication list 61 can be a list showing probability values of types of complications output from the classifier 53. For example, the server 1 determines whether a probability value of each type of complication output from the classifier 53 is equal to or greater than a predetermined threshold. The server 1 outputs names (types) of the complications determined to be equal to or greater than the threshold and the probability values of the complications as the complication list 61.

The occurrence condition list 62 is a list showing occurrence conditions of a complication output from the classifier 53. For example, the display apparatus 23 receives specified input for specifying the names (types) of the complications whose occurrence conditions are displayed for the complication list 61. Then, the display apparatus 23 displays estimated values of the occurrence conditions of a specified complication in the occurrence condition list 62. Specifically, the display apparatus 23 can display the inflated diameter, the inflated pressure, the inflated time, and the like of the balloon in which the complication is highly likely to occur.

The countermeasure information column 63 is a display column that displays countermeasure information for the complications. For example, similarly to the occurrence condition list 62, when the specified input of the names of the complications is received in the complication list 61, the display apparatus 23 displays the countermeasure information for the specified complications in the countermeasure information column 63.

The countermeasure information is information indicating a method of preventing the complications, and can be, for example, information indicating a treatment device that is effective for preventing the complications or a method of using the treatment device. According to the complication information output from the classifier 53, the server 1 reads the countermeasure information on the complication having a high probability value from the countermeasure information DB 141, and outputs the countermeasure information to the display apparatus 23. For example, the server 1 outputs the countermeasure information indicating another treatment device effective for preventing the complications, and proposes the user to use the devices in combination or substitute for another device.

The countermeasure information may be not only a method for preventing the complications, but also a countermeasure method that can be taken after the complications occur.

Further, the display apparatus 23 displays the tomographic image 64 generated by the intravascular diagnostic imaging apparatus 21 and the fluoroscopic image 65 captured by the fluoroscopic image capturing apparatus 22. In this case, the display apparatus 23 displays the second medical image obtained by processing the dangerous region of the original medical image as the tomographic image 64 and the fluoroscopic image 65. Specifically, as described above, the display apparatus 23 displays the second medical image indicating the dangerous region in a display mode different from that of the other image regions by superimposing the semitransparent mask on the dangerous region.

Although a two-dimensional tomographic image and a two-dimensional fluoroscopic image are shown as the second medical image in FIG. 6, the server 1 may also reconstruct the two-dimensional tomographic image and the two-dimensional fluoroscopic image, generate a three-dimensional blood vessel image, and display the three-dimensional blood vessel image on the display apparatus 23. As described above, the server 1 sequentially inputs a plurality of tomographic images (transverse tomographic images) sequentially acquired from the intravascular diagnostic imaging apparatus 21 and the fluoroscopic image into the training model 50, to generate, as the second medical images, a plurality of tomographic images and a fluoroscopic image obtained by processing the dangerous region. The server 1 performs position alignment between the tomographic images and the fluoroscopic image according to a position of the catheter 211 detected by units such as the X-ray opaque marker, and generates the three-dimensional blood vessel image. Accordingly, the dangerous region in which the complication is likely to occur in the blood vessel can be represented in three dimensions and presented to the user.

Figure 7:
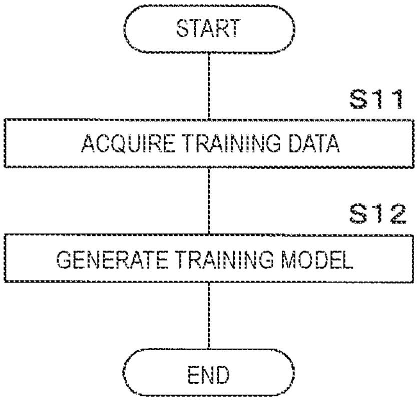
FIG. 7 is a flowchart showing a procedure of generation processing of the training model.

FIG. 7 is a flowchart showing a procedure of generation processing of the training model 50. Based on FIG. 7, processing contents when the training model 50 is generated by machine learning will be described. The control unit 11 of the server 1 acquires training data including the medical image for training and the correct complication information (S11). For example, the control unit 11 acquires the training data in which the label data indicating the type of the occurred complication, the occurrence conditions, the region (dangerous region) in the medical image in which the complication occurs, and the like are assigned to the medical image of the patient in whom the complication occurs after the treatment.

Based on the training data, the control unit 11 generates the training model 50 that outputs the complication information on the complication that is likely to occur after the treatment when the medical image is input (S12). For example, as described above, the control unit 11 generates a neural network related to the CNN as the training model 50. The control unit 11 inputs the medical image for training into the training model 50 and acquires the complication information as output. The control unit 11 compares the output complication information with the correct complication information, and optimizes a parameter such as the weight between the neurons so that the two pieces of complication information are approximate to each other to generate the training model 50. The control unit 11 ends the series of processing.

Figure 8:
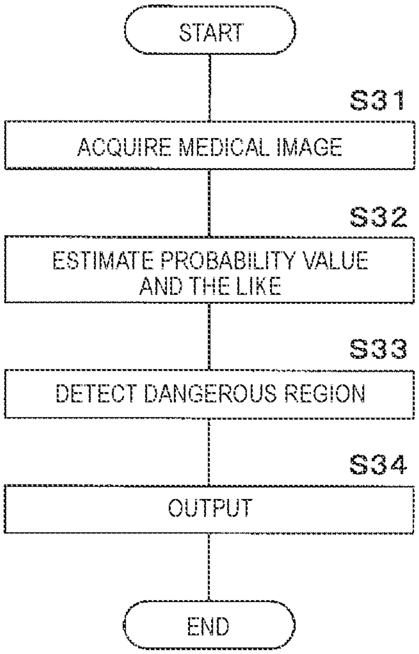
FIG. 8 is a flowchart showing a procedure of output processing of the complication information.

FIG. 8 is a flowchart showing a procedure of output processing of the complication information. Based on FIG. 8, processing contents when the complication information on the patient to be treated is output using the training model 50 will be described. The control unit 11 of the server 1 acquires the medical image obtained by imaging the blood vessel of the patient to be treated from the diagnostic imaging system 2 (S31). The control unit 11 inputs the acquired medical image into the training model 50, and estimates the probability value and the occurrence conditions of each of the plurality of types of complications that are assumed (S32).

The control unit 11 detects the dangerous region in which the complication is likely to occur based on the medical image acquired in S11 (S33). The control unit 11 generates the second medical image indicating the dangerous region detected in S33 in addition to the probability value and the occurrence conditions of the complication estimated in S32, the countermeasure information on the complication having the probability value equal to or greater than the threshold, and the like, outputs them to the display apparatus 23, and causes the display apparatus 23 to display them (S34). The control unit 11 ends the series of processing.

Only the medical image is used as the input into the training model 50 in the above description, but the present embodiment is not limited to only using the medical image as the input into the training model 50. For example, the server 1 may use, in addition to the medical image, the information on the balloon, the stent, and the like as the treatment device (diameter and length of stent, type and length of balloon, and the like) for input. Accordingly, based on the information on the treatment device itself, it is possible to suitably estimate the use conditions having a high possibility that the complication is likely to occur when the device is used. In addition, for example, the server 1 may use medical care information (for example, age, gender, and past medical history) on a patient to be treated for input. In this way, the input into the training model 50 is not limited to images.

As described above, according to the first embodiment, it is possible to suitably evaluate the risk of the complication by using the training model 50 that completes learning the training data.

According to the first embodiment, it is possible to present the complication that is highly likely to occur to the user by outputting the type and the probability value of the complication that is likely to occur.

According to the first embodiment, it is possible to more suitably support performing the treatment by outputting the countermeasure information for the complication as well.

According to the first embodiment, it is possible to more suitably support prevention of the complication by outputting the occurrence conditions of the complication, such as the treatment device that may cause the complication and the use conditions (expansion conditions) of the treatment device.

According to the first embodiment, by outputting the second medical image indicating the dangerous region in which the complication is likely to occur, it is possible to suitably grasp a portion in which the complication is likely to occur.

Second Embodiment

In the present embodiment, an embodiment will be described in which only an intravascular tomographic image is used as a medical image. The same contents as those of the first embodiment are denoted by the same reference numerals, and descriptions of the same contents as those of the first embodiment will be omitted.

Figure 9:
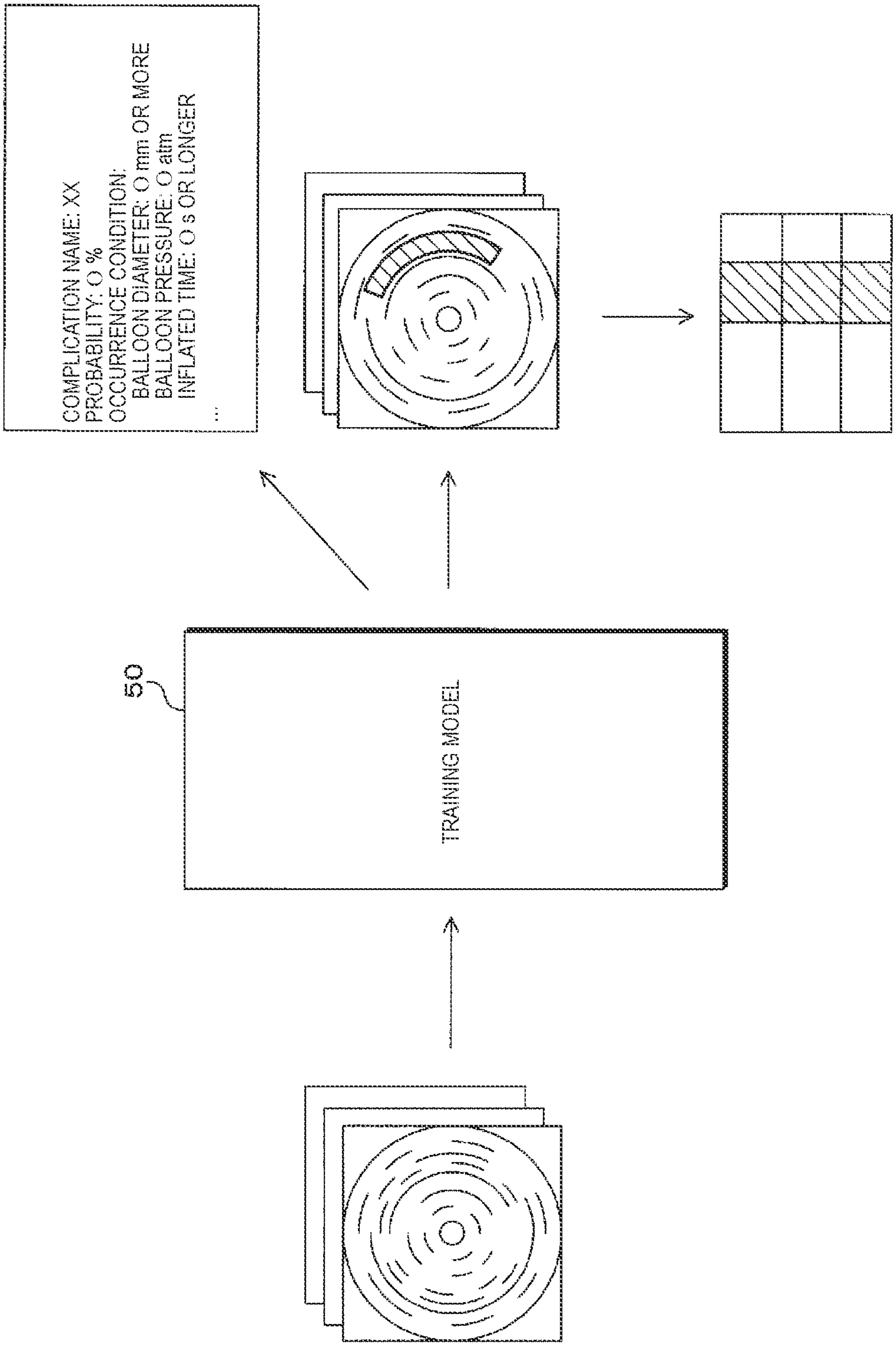
FIG. 9 is a diagram illustrating an outline of a training model according to a second embodiment.

FIG. 9 is a diagram illustrating an outline of the training model 50 according to a second embodiment. As shown in FIG. 9, the training model 50 according to the present embodiment uses only tomographic images acquired from the intravascular diagnostic imaging apparatus 21 as medical images as input. Specifically, the training model 50 receives, as the input, the tomographic images of a plurality of consecutive frames along a longitudinal direction of a blood vessel, and outputs an estimation result such as a probability value of a complication and a detection result of a dangerous region in the tomographic images of the frames. For example, in the training model 50, the second encoder 52 and the second decoder 55 are removed from the network structure illustrated in FIG. 5, and only the first encoder 51, the classifier 53, and the first decoder 54 are used. The training model 50 outputs prediction results of the classifier 53 and the first decoder 54 as complication information.

Figure 10:
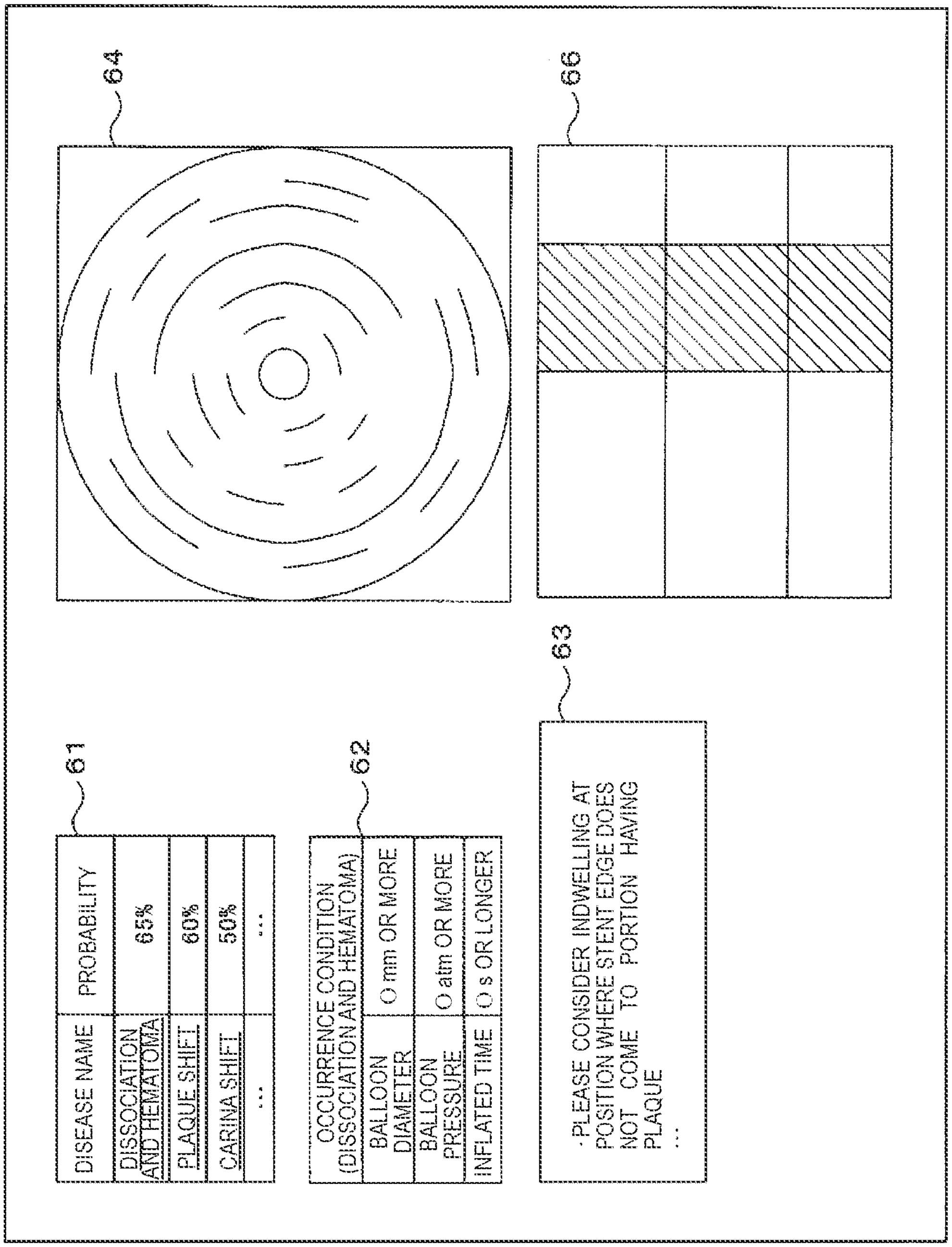
FIG. 10 is a diagram illustrating an example of a display screen that displays complication information according to the second embodiment.

FIG. 10 is a diagram illustrating an example of a display screen that displays the complication information according to the second embodiment. In the present embodiment, similarly to the first embodiment, the display apparatus 23 displays the complication list 61, the occurrence condition list 62, the countermeasure information column 63, and the tomographic image 64. The display apparatus 23 further displays a vertical tomographic image 66.

The vertical tomographic image 66 is an image obtained by imaging a cross section of the blood vessel parallel to the longitudinal direction, and is a tomographic image in which a direction of the cross section is orthogonal to that of a transverse tomographic image. The server 1 reconstructs transverse tomographic images of a plurality of frames generated by the intravascular diagnostic imaging apparatus 21, generates the vertical tomographic image 66 along the longitudinal direction of the blood vessel, and displays the vertical tomographic image 66 on the display apparatus 23.

In this case, similarly to the tomographic image 64 (transverse tomographic image), the server 1 generates the vertical tomographic image 66 in which the dangerous region can be identified, and causes the display apparatus 23 to display the vertical tomographic image 66. For example, as shown by hatching in FIG. 10, the server 1 generates the vertical tomographic image 66 in which a semitransparent mask is superimposed on a portion corresponding to the dangerous region, and causes the display apparatus 23 to display the vertical tomographic image 66.

For example, the server 1 identifies the dangerous region in the vertical tomographic image 66 based on the detection result of the dangerous region in each of the plurality of transverse tomographic images serving as a basis of the vertical tomographic image 66. That is, when the dangerous region is detected from the plurality of continuous transverse tomographic images, the server 1 identifies a region of the vertical tomographic image 66 corresponding to each transverse tomographic image as the dangerous region, and superimposes the semitransparent mask thereon. The server 1 outputs, to the display apparatus 23, the vertical tomographic image 66 processed so that the dangerous region can be identified, and causes the display apparatus 23 to display the vertical tomographic image 66.

Since the second embodiment is the same as the first embodiment except for the above points, a detailed description of a flowchart and the like is omitted in the present embodiment.

Third Embodiment

In the present embodiment, an embodiment will be described in which correction input for correcting complication information output from the training model 50 is received from a user, and relearning is performed based on the corrected complication information.

Figure 11:
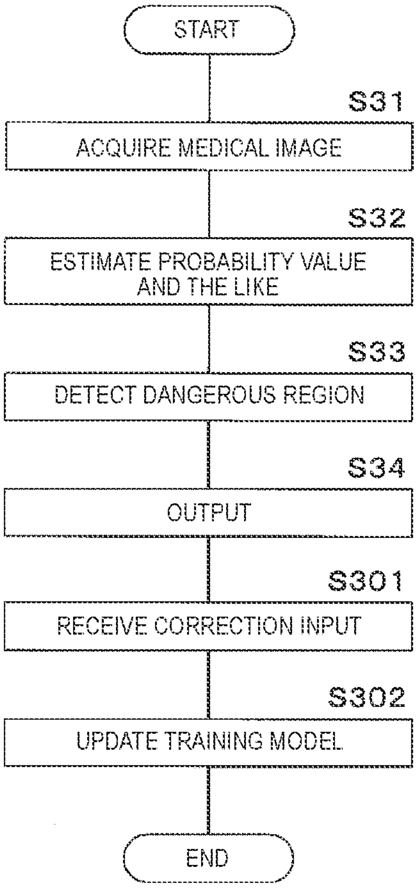
FIG. 11 is a flowchart showing a procedure of output processing of complication information according to a third embodiment.

FIG. 11 is a flowchart showing a procedure of output processing of complication information according to a third embodiment. After outputting the complication information (S34), the server 1 executes the processing as follows. The control unit 11 of the server 1 receives, from the user, the correction input of the complication information output to the display apparatus 23 (S301). For example, the control unit 11 receives the correction input for correcting the information of each item displayed in the complication list 61 and the occurrence condition list 62 on the display screen illustrated in FIG. 6. When a coordinate range of a dangerous region is different from an actual coordinate range with respect to a second medical image displayed as the tomographic image 64 and the fluoroscopic image 65, the server 1 receives specified input for specifying a correct coordinate range.

When the correction input of the complication information is received, the control unit 11 uses a medical image input into the training model 50 and the corrected complication information as training data to perform the relearning, and updates the training model 50 (S302). That is, the control unit 11 updates a parameter such as a weight between neurons so that the complication information output from the training model 50 approximates to the corrected complication information. The control unit 11 ends the series of processing.

As described above, according to the third embodiment, it is possible to update the training model 50 through operations of the present system and improve estimation accuracy of the complication information.

The detailed description above describes embodiments of a program, an information processing method, an information processing device, and a model generating method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium (CRM) storing computer program code executed by a computer processor that executes a process comprising:

acquiring a medical image obtained by imaging a lumen organ of a patient before a percutaneous coronary intervention (PCI) treatment;

inputting the acquired medical image into a trained model that has learned to output complication information on a complication that is likely to occur after the PCI treatment;

outputting, by the trained model, the complication information, wherein the complication information includes a type of complication that is likely to occur and an occurrence condition list, the occurrence condition list showing the type of complication that is likely to occur after the PCI treatment with a use condition of a treatment device to be inserted into the lumen organ under which the type of complication is likely to occur, and wherein the use condition of the treatment device during the PCI treatment includes two or more of an inflated diameter of a balloon of a balloon catheter, an inflated pressure of the balloon of the balloon catheter, and an inflated time of the balloon of the balloon catheter; and displaying the complication information on a display screen.

2. The computer-readable medium according to claim 1, further comprising:

outputting the complication information that includes the type of the complication that is likely to occur and a probability value indicating an occurrence probability of the complication of the type.

3. The computer-readable medium according to claim 2, further comprising:

outputting countermeasure information that indicates a countermeasure against the complication that is likely to occur according to the complication information.

4. The computer-readable medium according to claim 1, wherein the lumen organ is a blood vessel, and further comprising:

outputting an expansion condition of the blood vessel by the treatment device as the occurrence condition.

5. The computer-readable medium according to claim 1, further comprising:

detecting a dangerous region in which a complication is likely to occur based on the medical image by using the trained model; and outputting a second medical image indicating the detected dangerous region.

6. The computer-readable medium according to claim 1, further comprising:

acquiring a tomographic image obtained by imaging inside of the lumen organ and a fluoroscopic image of inside of a body of the patient; and inputting the tomographic image and the fluoroscopic image into the trained model and outputting the complication information.

7. The computer-readable medium according to claim 1, further comprising:

acquiring a plurality of continuous transverse tomographic images along a longitudinal direction of the lumen organ; and inputting the plurality of transverse tomographic images into the trained model and outputting the complication information.

8. The computer-readable medium according to claim 7, further comprising:

detecting the dangerous region in which the complication is likely to occur from each of the plurality of transverse tomographic images by using the trained model; and generating a vertical tomographic image indicating the dangerous region based on a detection result of the dangerous region in each of the plurality of transverse tomographic images.

9. The computer-readable medium according to claim 1, further comprising:

receiving correction input of the output complication information; and updating the trained model based on the medical image and the corrected complication information.

10. The computer-readable medium according to claim 1, wherein the medical image includes one or more of an ultrasound tomographic image, an optical coherence tomographic image, a fluoroscopic image, and a magnetic resonance imaging image of the lumen organ.

11. The computer-readable medium according to claim 1, further comprising:

inputting information on the treatment device into the trained model, and wherein the treatment device is the balloon catheter.

12. The computer-readable medium according to claim 1, wherein the trained model is trained with training data to which correct complication information is assigned as a label data on the medical image for training, the label data indicating the type of the complication that occurs in a plurality of patients, occurrence conditions when the complication occurs in the plurality of patients, and a region in the medical image in which the complication occurs in the plurality of patients.

13. An information processing apparatus comprising:

a processing server configured to:

acquire a medical image obtained by imaging a lumen organ of a patient before a percutaneous coronary intervention (PCI) treatment;

input the acquired medical image into a trained model that is learned to output complication information on a complication that is likely to occur after the PCI treatment; and output, by the trained model, the complication information, wherein the complication information includes a type of complication that is likely to occur and an occurrence condition list, the occurrence condition list showing the type of complication that is likely to occur after the PCI treatment with a use condition of a treatment device to be inserted into the lumen organ under which the type of complication is likely to occur, the use condition of the treatment device during the PCI treatment including two or more of an inflated diameter of a balloon of a balloon catheter, an inflated pressure of the balloon of the balloon catheter, and an inflated time of the balloon of the balloon catheter; and a display screen configured to display the complication information.

14. A model generation method executed by a computer, the model generation method comprising:

acquiring training data including a medical image obtained by imaging a lumen organ of a patient before a percutaneous coronary intervention (PCI) treatment and complication information on a complication that occurs after the PCI treatment; and generating, based on the training data, a trained model that outputs the complication information when the medical image is received, wherein the complication information includes a type of complication that is likely to occur and an occurrence condition list, the occurrence condition list showing the type of complication that is likely to occur after the PCI treatment with a use condition of a treatment device to be inserted into the lumen organ under which the type of complication is likely to occur, the use condition of the treatment device during the PCI treatment including two or more of an inflated diameter of a balloon of a balloon catheter, an inflated pressure of the balloon of the balloon catheter, and an inflated time of the balloon of the balloon catheter.

15. The model generation method according to claim 14, further comprising:

outputting the complication information that includes the type of the complication that is likely to occur and a probability value indicating an occurrence probability of the complication of the type.

16. The model generation method according to claim 15, further comprising:

outputting countermeasure information that indicates a countermeasure against the complication that is likely to occur according to the complication information.

17. The model generation method according to claim 14, wherein the lumen organ is a blood vessel, and further comprising:

outputting an expansion condition of the blood vessel by the treatment device as the occurrence condition.

18. The model generation method according to claim 14, further comprising:

detecting a dangerous region in which the complication is likely to occur based on the medical image by using the model; and outputting a second medical image indicating the detected dangerous region.

19. The model generation method according to claim 14, further comprising:

inputting information on the treatment device into the trained model, and wherein the treatment device is the balloon catheter.

20. The model generation method according to claim 14, wherein the trained model is trained with training data to which correct complication information is assigned as a label data on the medical image for training, the label data indicating the type of the complication that occurs in a plurality of patients, occurrence conditions when the complication occurs in the plurality of patients, and a region in the medical image in which the complication occurs in the plurality of patients.

* * * * *